US012496407B2

(12) United States Patent
Wang et al.

(10) Patent No.: US 12,496,407 B2
(45) Date of Patent: Dec. 16, 2025

(54) DRUG DELIVERY DEVICE

(71) Applicant: Gangan Medical Technology Jiangsu Co., Ltd., Jiangsu (CN)

(72) Inventors: Chunsheng Wang, Jiangsu (CN); Lihua Zhou, Jiangsu (CN)

(73) Assignee: Gangan Medical Technology Jiangsu Co., Ltd., Jiangsu (CN)

( * ) Notice: Subject to any disclaimer, the term of this patent is extended or adjusted under 35 U.S.C. 154(b) by 525 days.

(21) Appl. No.: 18/043,806

(22) PCT Filed: Sep. 2, 2021

(86) PCT No.: PCT/CN2021/116298

§ 371 (c)(1), (2) Date: Mar. 2, 2023

(87) PCT Pub. No.: WO2022/048606

PCT Pub. Date: Mar. 10, 2022

(65) Prior Publication Data

US 2023/0338665 A1 Oct. 26, 2023

(30) Foreign Application Priority Data

Sep. 3, 2020 (CN) ......................... 202010917227.8

(51) Int. Cl.
*A61M 5/315* (2006.01)
*A61M 5/20* (2006.01)

(52) U.S. Cl.
CPC .......... *A61M 5/31551* (2013.01); *A61M 5/20* (2013.01); *A61M 5/315* (2013.01)

(58) Field of Classification Search
CPC .... A61M 5/31551; A61M 5/20; A61M 5/315; A61M 5/31563; A61M 5/31541
See application file for complete search history.

(56) References Cited

U.S. PATENT DOCUMENTS

2004/0210199 A1 10/2004 Atterbury et al.
2006/0206057 A1 9/2006 DeRuntz et al.
(Continued)

FOREIGN PATENT DOCUMENTS

CN 104338210 A 2/2015
CN 110141727 A 8/2019
(Continued)

OTHER PUBLICATIONS

International Search Report issued Nov. 30, 2021 in PCT/CN2021/116298.

*Primary Examiner* — Dung T Ulsh
(74) *Attorney, Agent, or Firm* — Ice Miller LLP

(57) ABSTRACT

This application provides a drug delivery device. The drug delivery device comprises a housing, a driving mechanism, a first limiting structure, an injection mechanism and a transmission mechanism. The driving mechanism comprises a adjusting member, a first memory and a second memory. When the driving mechanism is in the adjusting state, the adjusting member drives the second memory to move between the initial position and the end position. When the driving mechanism is in the delivery state, the adjusting member, the first memory and the second memory are relatively static. One of the first limit member and the second limit member of the first limiting structure is arranged on the first memory, and the other of the first limit member and the second limit member is arranged on the second memory. The first limit member and the second limit member are cooperated to limit the movement of the second memory relative to the first memory when the second memory arrives at the end position. The delivery device can resolve the problem in the related art that it is difficult to prevent a set dose from exceeding the remaining dose in the medicine bottle.

12 Claims, 7 Drawing Sheets

(56) References Cited

U.S. PATENT DOCUMENTS

| | | | | |
|---|---|---|---|---|
| 2015/0065963 | A1* | 3/2015 | Kjeldsen | A61M 5/31501 604/207 |
| 2015/0224266 | A1 | 8/2015 | Plumptre et al. | |
| 2016/0193421 | A1* | 7/2016 | Bayer | A61M 5/3158 604/208 |
| 2018/0140776 | A1* | 5/2018 | Bengtsson | A61M 5/31581 |
| 2018/0289895 | A1* | 10/2018 | Windum | A61M 5/31553 |
| 2019/0125977 | A1 | 5/2019 | Wang | |

FOREIGN PATENT DOCUMENTS

| | | | |
|---|---|---|---|
| CN | 110215573 | A | 9/2019 |
| CN | 110269977 | A | 9/2019 |
| CN | 210542653 | U | 5/2020 |
| CN | 111437468 | A | 7/2020 |
| CN | 212395535 | U | 1/2021 |
| WO | 2016201586 | A1 | 12/2016 |

* cited by examiner

DRUG DELIVERY DEVICE

CROSS-REFERENCE TO RELATED APPLICATION

This application is a Section 371 of International Application No. PCT/CN2021/116298 filed Sep. 2, 2021, which was published in the Chinese language Mar. 10, 2022, under International Publication No. WO 2022/048606 A1, which claims priority to Chinese Patent Application No. 202010917227.8 filed Sep. 3, 2020, the disclosures of which are incorporated herein by reference in their entireties.

TECHNICAL FIELD

The present disclosure relates to the technical field of injection device, and particularly to a drug delivery device.

BACKGROUND ART

Currently, patients who need to self-administer medication are usually injected with a self-administered injection device, which is commonly driven by a threaded rod to achieve injection of medication. During use, the user performs injection by rotating the adjusting member to a desired dose, then inserting the needle of the injector into the body and finally pushing the button which drives the movement of threaded rod to achieve the injection.

However, regarding the related device in the prior art, the situation often occurs that when the amount of remaining medication in the bottle installed in the injection device is less than the required injection dose, patients still can rotate the adjusting member to adjust the scale value, which cannot remind the patients remaining dose in the medicine bottle is not enough, which causes patients to not know the amount of drug injected this time, resulting in a safety hazard. Therefore, Technical problems of difficulty to prevent a set dose from exceeding the remaining dose in the medicine bottle exist in the related art.

SUMMARY

The present application provides a drug delivery device to solve the problem in the related art that it is difficult to prevent the set dose from exceeding the remaining dose in the medicine container.

The present application provides a drug delivery device. The drug delivery device comprises: a housing; a driving mechanism arranged in the housing, comprising a adjusting member, a first memory and a second memory cooperating to the first memory. The second memory has an initial position and an end position relative to the first memory, and the driving mechanism has a adjusting state and a delivering state. When the driving mechanism is in the adjusting state, the adjusting member drives the second memory to move between the initial position and the end position. When the driving mechanism is in the delivering state, the adjusting member, the first memory and the second memory are relatively static; first limiting structure, comprising a first limit member and second limit member, one of the first limit member and the second limit member is arranged on the first memory, and the other of the first limit member and the second limit member is arranged on the second memory, the first limit member cooperates with the second limit member to limit the movement of the second memory relative to the first memory when the second memory is at the end position; an injection mechanism, used for injecting medication; a transmission mechanism, arranged between the driving mechanism and the injection mechanism; the driving mechanism drives the injection mechanism by the transmission mechanism to inject a dose.

Furthermore, the adjusting member is rotatably and axially movable in the housing, the first memory is arranged within the adjusting member, and the second memory is sleeved on the outer wall of the first memory and is threadedly cooperating with the first memory, and a first rotation-preventing structure is arranged between the second memory and the adjusting member so as to limit the rotation of the second memory relative to the adjusting member.

Furthermore, the first rotation-preventing structure comprises a first stop protrusion and a first stop groove, and one of the first stop protrusion and the first stop groove is arranged on the inner wall of the adjusting member, and the other of the first stop protrusion and the first stop groove is arranged on the outer wall of the second memory; the first stop protrusion is inserted in the first stop groove, and both of the first stop protrusion and the first stop groove extend along the axial direction of the adjusting member.

Furthermore, the first limit member is a first limit protrusion arranged on the one side of the first memory close to the end position, the second limit member is a second limit protrusion arranged on the one the side of the second memory close to the end position, and the first limit protrusion cooperates with the second limit protrusion in a snap-fit manner to limit the rotation of the second memory relative to the first memory.

Furthermore, the transmission mechanism comprises: a piston rod, is drivingly connected to the injection mechanism; a first transmission member is rotatably arranged in the housing, the driving mechanism is drivingly connected to the first transmission member, and the piston rod is arranged within the first transmission member, a second rotation-preventing structure is arranged between the piston rod and the first transmission member limits the rotation of the piston rod relative to first transmission member; a second transmission member is fixed in the housing, the piston rod is arranged within the second transmission member and threadedly cooperates with the second transmission member; a unidirectional rotation structure, arranged between the first transmission member and the second transmission member, the unidirectional rotation structure is used to limit the unidirectional rotation of first transmission member relative to the second transmission member.

Furthermore, the second transmission member has an opening, and the opening comprises a first segment and a second segment which are connected to each other, and the second segment faces the first transmission member, the first segment is provided with an internal thread cooperated with the piston rod and one end of the first transmission member is arranged within the second segment, wherein, the end of the first transmission member is provided with a reset member, the reset member is provided with first unidirectional teeth, and the inner wall of the second segment is provided with second unidirectional teeth, the reset member, the first unidirectional teeth and the second unidirectional teeth are cooperated to limit unidirectional rotation of the first transmission member relative to the second transmission member, or, the end of the first transmission member is provided with a first unidirectional teeth, the end wall of the first section is provided with a reset member, and the reset member is provided with second unidirectional teeth; the reset member, the first unidirectional teeth and the second unidirectional teeth cooperate to limit the unidirectional rotation of the first transmission member relative to the second transmission member.

Furthermore, the first transmission member is axially fixed to housing, the first memory coaxially and slidably sleeved on the outer wall of the first transmission member and the drug delivery device further comprising: the second limit structure, arranged between the first memory and the first transmission member, and the second limit structure is used to limit the position of the memory member relative to the first transmission member.

Furthermore, the second limit structure (80) comprises a third limit protrusion (81) arranged on the one of the first memory (22) and the first transmission member (52) and a limit groove (82) first transmission member set on the other of the first memory (22) and the first transmission member (52), the limit-groove (82) extends along the axial direction of the housing (10), and the third limit protrusion (81) is slidably arranged within the limit groove (82) and cooperates with the limit groove (82) to limit the relative displacement between first memory (22) and the first transmission member (52) in both the circumferential direction and axial direction.

Furthermore, the driving mechanism further comprises a clutch member arranged between the adjusting member and the first memory, one end of the clutch member is provided with a first tooth, and the other end of the clutch member is provided with a second tooth; and the adjusting member has a ring-protrusion arranged along the circumference of the adjusting member, the ring-protrusion is provided with a third tooth engaging with the first tooth, and the end wall of first memory is provided with a forth tooth engaging with the second tooth.

Furthermore, the drug delivery device further comprises an injection button arranged at the driving end of the housing, a n injection button connector arranged in the housing and between the button and the first memory, a resilient member arranged between the button and the connector and a medication container arranged at the injection end of the housing, the injection button is arranged at the driving end of the housing, and the injection button connector is arranged between the injection button (90) and the first memory in the housing, and the resilient member is arranged between the injection button and the injection button connector, the medication container is arranged at the injection end of the housing; the injection mechanism comprises a flange, the flange is movably arranged in the medication container, and the transmission mechanism is drivingly connected to the flange; the housing comprises a main housing and a sleeve arranged separately, or the main housing and the sleeve are integrally formed.

Applying the technical solution of the present application, the drug delivery device comprises a housing, a driving mechanism, a first limiting structure, an injection mechanism and a transmission mechanism. When using the drug delivery device to inject medicine: firstly, adjusting the adjusting member to a desired dose when the driving mechanism is at the adjusting state. During the process of adjusting a dose, the adjusting member drives the second memory to move between the initial position and the end position relative to the first memory followed by injecting a dose, during the injection process, the second memory is not moveable relative to the first memory, so as to achieve an injection memory. After multiple times of injections, when the amount of medicine in the medication container is less than the required injection dose, since the second memory has moved a distance from the initial position towards the end position successively in each process of previous injections, at this time, in the process that adjusting member is adjusted to a desired dose, when the second memory arrives at the end position during dose setting, the second memory cannot further move relative to the first memory due to limitation by the first rotation-preventing structure, accordingly, patients cannot further adjust the adjusting member, so as to prevent the set dose from exceeding the remaining dose in the medication container, which reminds the patient that the medication dose in the medicine container is not enough for this injection. In addition, the way to limit the relative position between the first memory and the second memory by using the coordination between the first limit member 31 and the second limiting protrusion 32 shows a stable limiting effect.

BRIEF DESCRIPTION OF DRAWINGS

The accompanying drawings constituting a part of the present disclosure are used to provide a further understanding of the present application and, and the illustrative Embodiments of the present disclosure and the description thereof are used to explain the present application and do not constitute an improper limitation of the present application. In the accompanying drawings.

Figure 1:
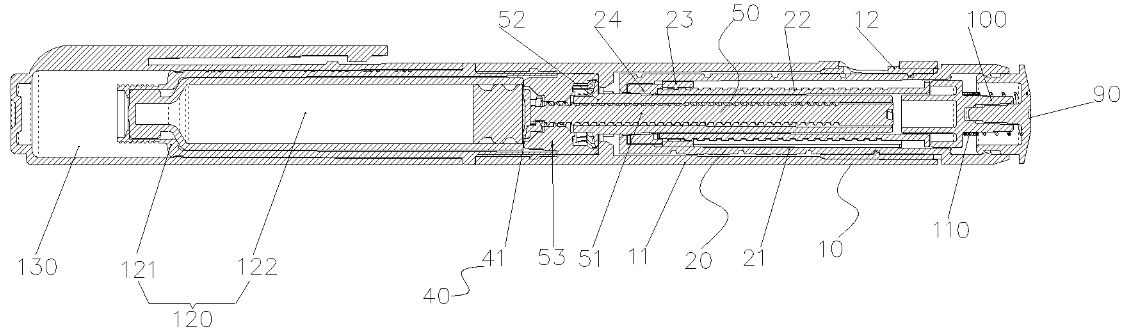
FIG. 1 shows a structural schematic diagram of the drug delivery device provided in accordance with Embodiment 1 of this application.

Wherein, the above-mentioned accompanying drawings include the following reference signs:

10. housing; 11. main housing; 12. Sleeve; 13. first ring-protrusion;

20. driving mechanism; 21. adjusting member; 211. ring-protrusion; 212. third tooth; 22. first memory; 221. fourth tooth; 23. second memory; 231. inner thread of second memory; 24. clutch member; 241. first tooth; 242. second tooth;

30. first limiting structure; 31. first limit member; 32. second limit member;

40. injection mechanism; 41. Flange;

50. transmission mechanism; 51. piston rod; 52. first transmission member; 521. reset member; 522. first unidirectional teeth; 523. oblong hole; 524. second ring-protrusion; 53. second transmission member; 531. hole; 532. inner thread of second transmission member; 533. second unidirectional teeth; 54. unidirectional rotation structure;

60. first rotation-preventing structure; 61. first stop protrusion; 62. first stop groove;

70. second rotation-preventing structure;

80. second limit structure; 81. third limit-protrusion; 82. limit-groove; 821. end wall;

90. injection button; 100. injection button connector; 110. resilient member; 120. medication container; 121. medicine bottle holder; 122. medicine bottle; 130. pen cap

DETAILED DESCRIPTION OF EMBODIMENTS

Technical solutions of the present disclosure will be described below clearly and comprehensively with reference to accompanying drawings. Apparently, the described embodiments are only a part of embodiments of the present disclosure, rather than all embodiments of the present disclosure. The following description of at least one exemplary embodiment is in fact merely illustrative and is not intended as any limitation of the present application and its application or use. All other embodiments obtained by a person ordinarily skilled in the art based on the embodiments of the present disclosure without any inventive effort shall fall into the scope of protection of the present disclosure.

As illustrated in FIG. 1 to FIG. 15, a drug delivery device provided in the embodiment 1 of present disclosure comprises: a housing 10, a driving mechanism 20, a first limiting structure 30, an injection mechanism 40 and a transmission-mechanism 50, the injection mechanism 40 is used to inject the medicine, the transmission-mechanism 50 is provided between the driving mechanism 20 and the injection mechanism 40, the driving mechanism 20 drives the injection mechanism 40 to inject by transmission-mechanism 50.

In the above, the driving mechanism 20 is provided within housing 10, driving mechanism 20 comprises adjusting member 21, first memory 22 and second memory 23 cooperating with the first memory 22, driving mechanism 20 has an adjustment state and a delivery state, second memory 23 has an initial position and an end position and it can move between two positions relative to first memory 22. When the driving mechanism 20 is in the adjusting state, adjusting member 21 drives second memory 23 to move between the initial position and the end position, while the driving mechanism 20 is in the delivery state, the adjusting member 21, first memory 22 and second memory 23 are stationary relative to each other. With the above structure, the second memory moves relative to the first memory when the dose is adjusted, and the second memory is stationary relative to the first memory when the drug is delivered, the second memory starts from the initial position and moves successively to the end position during multiple delivery processes. Specifically, first limiting structure 30 comprises first limit member 31 and second limit member 32, one of first limit member 31 and second limit member 32 being provided on first memory 22 and the other of them being provided on second memory 23, first limit member 31 cooperating with second limit member 32 to limit the movement of second memory 23 relative to first memory 22 when second memory 23 is in the end position, thus being able to prevent the movement of adjusting member 21.

With the drug delivery device provided by the present embodiment, the second memory 23 is located in the initial position when the drug delivery device is used for the first time, and the second memory 23 arrives at the end position at the time drug in the medication container exhausts after multiple delivery processes, thus preventing the set dose from exceeding the remaining dose in the medicine bottle.

Figure 3:
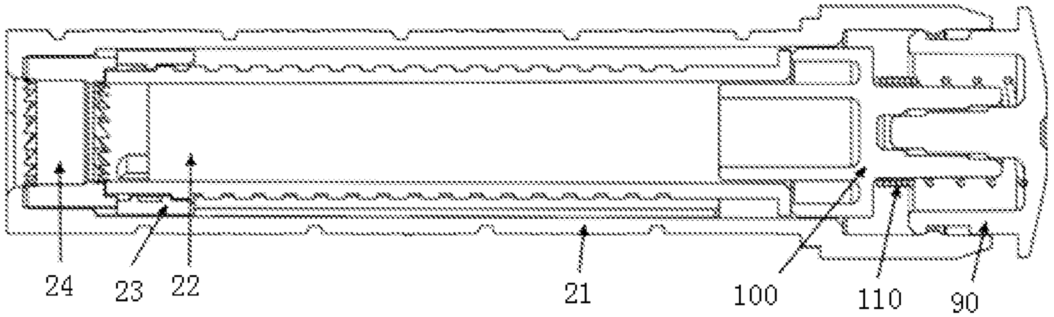
FIG. 3 shows a structural schematic diagram of the driving mechanism in FIG. 1.
Figure 4:
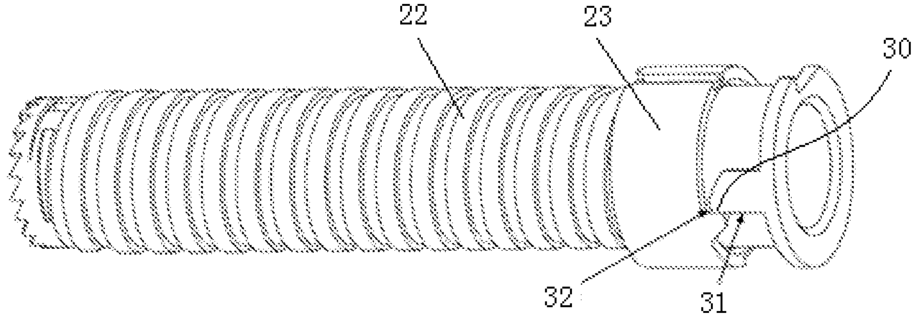
FIG. 4 shows an assembly drawing of the first memory and the second memory of the drug delivery device provided in accordance with Embodiment 1 of this application.

As illustrated in FIG. 3 and FIG. 4, the second memory 23 is located in the initial position and the end position respectively. When the dose is adjusted, driven by adjusting member, the second memory moves relative to the first memory, while the second memory is stationary relative to the first memory when the medication is delivered. During multiple delivery processes, the second memory moves from the initial position to the end position successively, and the medication in medication container is just exhausted when second memory arrives at the end position.

Specifically, when injecting drug by the drug delivery device, the adjusting member 21 is adjusted to the desired scale, and the adjusting member 21 drives the second memory 23 to move relative to the first memory 22 from the initial position to the end position, then perform injection after adjusting the scale. When delivering a dose, the second memory 23 is stationary relative to the first memory 22, thereby achieving an injection memory. After multiple delivery processes, if the dose in the medicine container is less than the desired dose, due to the second memory 23 will move from the initial position to the end position for a distance after each previous injection, in the process of adjusting the adjusting member 21 to corresponding scale of desired dose, when the second memory 23 arrives at the end position, the second memory 23 could not further move relative to the first memory 22 due to first limiting structure 30 to prevent the adjusting member 21 from further adjusting the dose, thereby realizing the memory function, and then it can remind patients that the dosage in the drug container is not enough for this injection. Furthermore, the way to limit the relative position between the first memory 22 and the second memory 23 by using the coordination between the first limit member 31 and the second limiting protrusion 32 shows a stable limiting effect.

Figure 6:
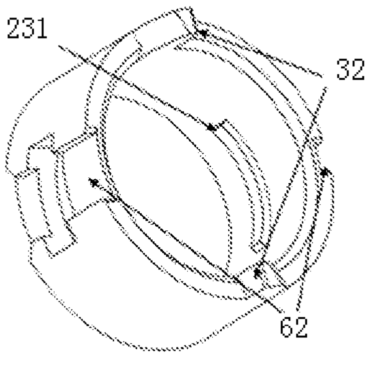
FIG. 6 shows a structural schematic diagram of the second memory in FIG. 1.
Figure 7:
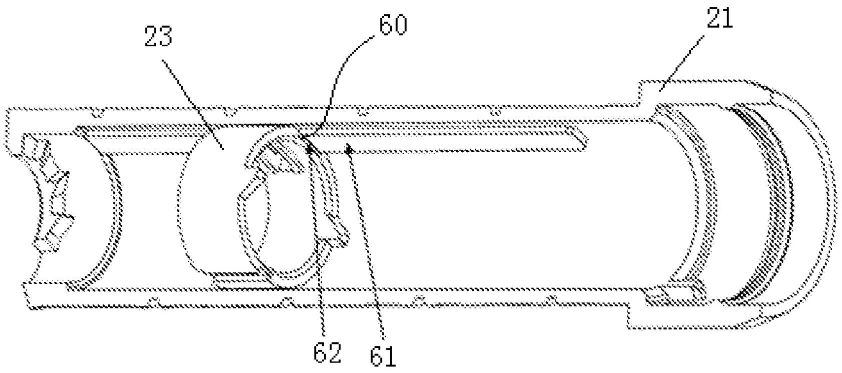
FIG. 7 shows an assembly drawing of the adjusting member and the second memory of the drug delivery device provided in accordance with Embodiment 1 of this application.

As illustrated in FIGS. 3,6 and 7, the adjusting member 21 is rotatable and axially movable within the housing 10, the adjusting member 21 has an opening, the first memory 22 is arranged in the opening of the adjusting member 21, and the second memory 23 locates between the outer surface of the first memory 22 and the inner surface of the adjusting member 21. Specifically, the second memory 23 is disposed on the outer surface of the first memory 22 and cooperates with the threads of first memory 22. In the present embodiment, a first rotation-preventing structure 60 is provided between the second memory 23 and the adjusting member 21. The first rotation-preventing structure 60 can prevent the rotation of the second memory 23 relative to the adjusting member 21, and then in the process of rotating he adjusting member, the adjusting member 21 will drive rotation of the second memory 23 along the first memory 22, resulting in the axial movement of the second memory 23. In the present embodiment, the inner surface of the second memory 23 is provided with inner threads 231.

In the present embodiment, adjusting member 21 is matched with the housing 10 through the thread. During rotation of adjusting member 21, adjusting member 21 is axially displaced relative to the housing 10.

As illustrated in FIG. 7, the first rotation-preventing structure 60 comprises the first stop protrusion 61 and the first stop groove 62, one of the first stop protrusion 61 and the first stop groove 62 being provided on the inner surface of adjusting member 21, and the other one of the first stop protrusion 61 and the first stop groove 62 being provided on the outer surface of second memory 23, the first stop protrusion 61 being inserted into the first stop groove 62, and both the first stop protrusion 61 and the first stop groove 62 extending in the axis of adjusting member 21. When the adjusting member 21 is rotated, with the engagement between the first stop protrusion 61 and the first stop groove 62, the second memory 23 follows the rotation of the adjusting member 21, and the threaded engagement between the second memory and the first memory allows the second memory to move axially along the axis of the first memory. In the present embodiment, the first stop protrusion 61 is provided on the inner surface of adjusting member 21 and the first stop groove 62 is provided on the outer surface of the second memory 23. In other embodiments, the first stop protrusion 61 can be provided on the outer surface of the second memory 23 and the first stop groove 62 is provided on the inner surface of the adjusting member 21.

In the above, the number of the first stop protrusion 61 and the first stop groove 62 can be one or more. In the present embodiment, two first stop protrusions 61 are provided symmetrically on the inner surface of the adjusting member 21 and two first stop grooves 62 are provided symmetrically on the outer surface of the second memory 23, where the first stop protrusion 61 locates at the corresponding engagement position of the first stop groove 62. The above-mentioned structure can not only improve the effect of preventing rotation, but also improve the stability of the second memory and the structure stability of the device.

In the above, the first limiting structure 30 comprises engagement structures of limit protrusions and limit protrusions, of limit protrusions and limit grooves, and of snaps and hooks.

Figure 5:
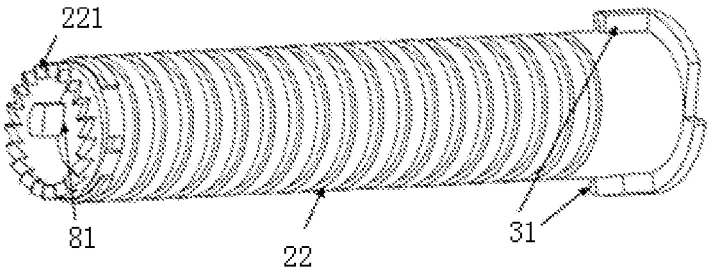
FIG. 5 shows a structural schematic diagram of the first memory in FIG. 1.

As illustrated in FIG. 4 to 6, in the present embodiment, the first limit member 31 is the first limit-protrusion and the second limit member 32 is a second limit-protrusion, the first limit protrusion is provided at one end of first memory 22 near the end position and the second limit protrusion is provided at one end of the second memory 23 near the end position, and when the second memory 23 moves from the initial position to the end position, the first limit protrusion cooperates with the second limit protrusion in a snap-fit manner to prevent the rotation of the second memory 23 relative to the first memory 22, thus reminding patients that the remaining dose in the medication container is not enough for injection.

In the present embodiment, multiple first limit protrusions are provided on the first memory and multiple first limit protrusions are provided on the second memory, where each of the first limit protrusions locates at the corresponding engagement position with each of second limit protrusions. Both effect and stability of limitation can be improved by the cooperation between multiple first limit protrusions and multiple second limit protrusions. In other embodiments, only one engagement between first limit protrusion and one second limit protrusion can also achieve the limiting function, simplifying the structure of the device.

In order to more clearly illustrate technical solutions of memory function, accompanying the using process will be introduced below.

(1) Initially, the second memory 23 is at the left end of the first memory 22 (initial position). There is a first stop protrusion 61 in the inner surface of the adjusting member 21, and a first stop groove 62 on the outer surface of the second memory 23, and the above protrusion 61 and groove 62 are locked in rotational direction, but permitting their relative axial movement. When increasing the dose, the rotation of adjusting member 21 in the first direction transmits the rotation of second memory 23. The second memory 23 is threadedly cooperated the first memory 22, and the first memory 22 does not rotate in the first direction, thus the second memory 23 moves relative to the first memory 22 in the right direction for a distance same as adjusting member 21. When decreasing the dose, the adjusting member 21 rotates in a second direction, and the second memory 23 moves relative to the first memory 22 in the left direction for a distance same as adjusting member 21.

(2) During injection, the second memory 23 has no relative movement with the first memory 22.

(3) The above process is repeated.

(4) During the final memory, the second memory 23 moves to the right end of the first memory 22 (end position), at this time, the first limit member and the second limit member are locked in the first direction, thus increasing the dose is prohibited. The amount of drug in the medication container is same as the scale of set dose. Accordingly, the amount of doses that had been delivered above is the maximum available doses, thus achieve the memory function. Of note, decreasing the dose is allowed at the moment.

As illustrated in FIG. 1, FIG. 8 to 10, transmission-mechanism 50 comprises piston rod 51, first transmission member 52, second transmission member 53, and unidirectional rotation structure 54. Piston rod 51 is driving-connected to injection mechanism 40. First transmission member 52 is rotatable provided inside of the housing 10. Driving mechanism 20 is driving-connected to first transmission member 52, and second transmission member 53 is fixed inside of the housing 10. Specifically, piston rod 51 is arranged in the first transmission member 52, and second rotation-preventing structure 70 is provided between piston rod 51 and first transmission member 52, where the second rotation-preventing structure 70 prevents piston rod 51 from rotating relative to first transmission member 52. When first transmission member 52 rotates, it transmits the rotational movement to piston rod 51 synchronously. Besides, piston rod 51 also moves axially since the piston rod 51 is threadedly cooperated the inner threads of second transmission member 53, thus driving injection mechanism 40 to deliver the doses.

Specifically, piston rod 51 is a non-circular rod, and the shape and size of its cross section matches the opening of first transmission member 52, thus forming second rotation-preventing structure 70. In the present embodiment, the piston rod comprises a flat surface, and the first transmission member has an oblong hole 523 to match the flat surface of the piston rod, which prohibits the piston rod rotational movement but allows rotational movement. In other embodiments, as long as the rotational limitation is able to be achieved, the engagement therebetween can be replaced with protrusions and grooves, or others.

In the present embodiment, unidirectional rotation structure 54 is provided between first transmission member 52 and second transmission member 53. The unidirectional rotation structure 54 can prevent the unidirectional rotation of first transmission member 52 relative to second transmission member 53, thus enabling the first transmission member, the piston rod and the first memory to rotate in only one direction of injection, so that achieving memory function.

Figure 8:
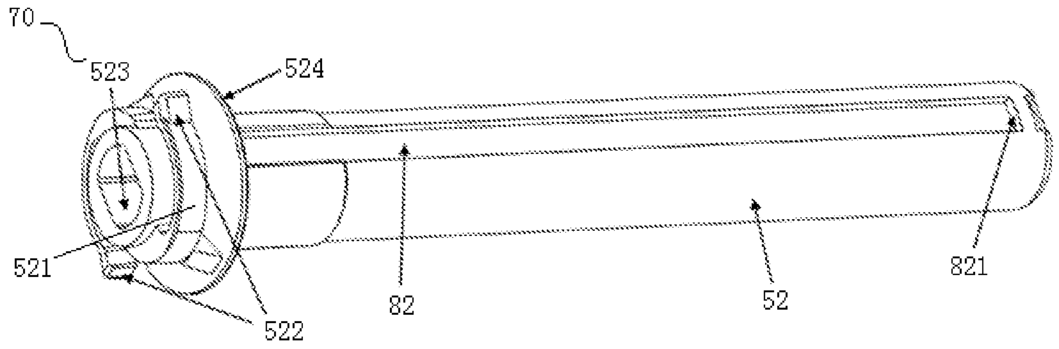
FIG. 8 shows a structural schematic diagram of the first transmission member in FIG. 1.
Figure 9:
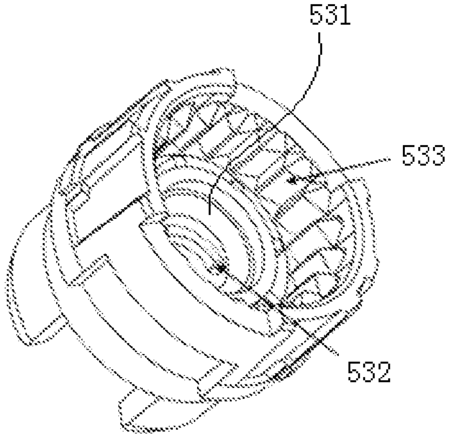
FIG. 9 shows a structural schematic diagram of the second transmission member in FIG. 1.
Figure 10:
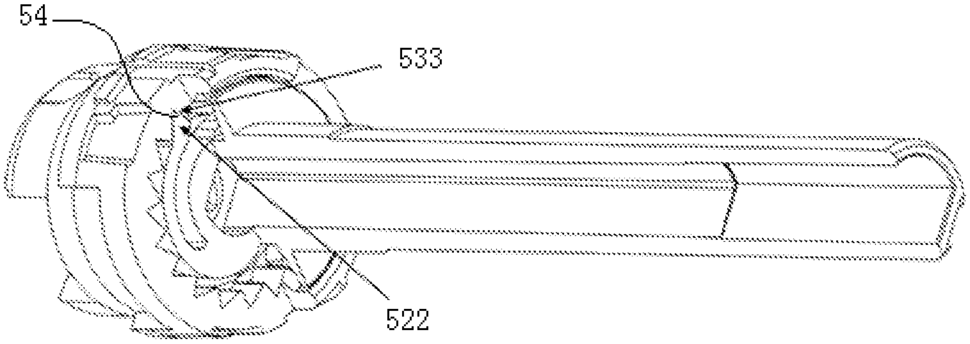
FIG. 10 shows an assembly drawing of the first transmission member and the second transmission member of the drug delivery device provided in accordance with Embodiment I of this application.

As illustrated in FIG. 8 to 10, second transmission member 53 comprises an opening 531, and the opening 531 comprises a first segment and a second segment that are connected to each other, where the second segment is set towards the first transmission member 52. Specifically, the first segment comprises inner thread 532 that is matched with piston rod 51, thus piston rod moves axially during its rotational movement. Specifically, one end of first transmission member 52 is arranged into the second segment, and one end of first transmission member 52 comprises a reset member 521, and the reset member 521 is movable in a radial direction relative to first transmission member 52. One end of reset member 521 comprises a unidirectional 522. The inner surface of the second segment comprises second unidirectional teeth 533. The rest member 521, first unidirectional teeth 522 and second one way teeth 533 are cooperated together to prevent first transmission member 52 from rotating relative to second transmission member 53, in other words, first transmission member 52 rotates unidirectionally relative to second transmission member 53. In the present embodiment, when second transmission member 53 is fixed, first transmission member 52 can rotate in the counterclockwise direction and is stuck in the clockwise direction, thus achieving unidirectional rotation function.

In the present embodiment, reset member 521 is a resilient arm, and one end of the resilient arm is connected to one end of the first transmission member 52, while the other end of the resilient arm is the free end, and the first unidirectional teeth 522 is provided on the free end of the resilient arm. In other embodiments, the reset member may be provided as other structures with resilience, as long as the reset member can be used to reset the first unidirectional teeth 522.

Specifically, a reset member (resilient arm) is provided on the side surface of one end of the first transmission member 52, with the resilient arm extending circumferentially along the first transmission member. Besides, the first unidirectional teeth 522 is provided on the resilient arm, and the second unidirectional teeth 533 is provided on the inner surface of the second segment of the central opening of second transmission member 53.

In the present embodiment, multiple reset members 521 are provided at the end of first transmission member 52, and multiple reset members 521 are positioned at intervals along the circumference of first transmission member 52, and a circle of second unidirectional teeth is provided along the circumference of the second transmission member, which locates on the inner surface of the second segment. Accordingly, multiple reset members function as rotation limitation to enhance its limiting effect.

Figure 14:
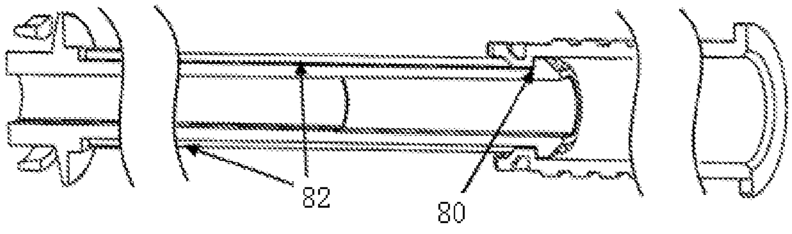
FIG. 14 shows an assembly drawing of the first transmission member and the first memory of the drug delivery device provided in accordance with Embodiment 1 of this application.
Figure 15:
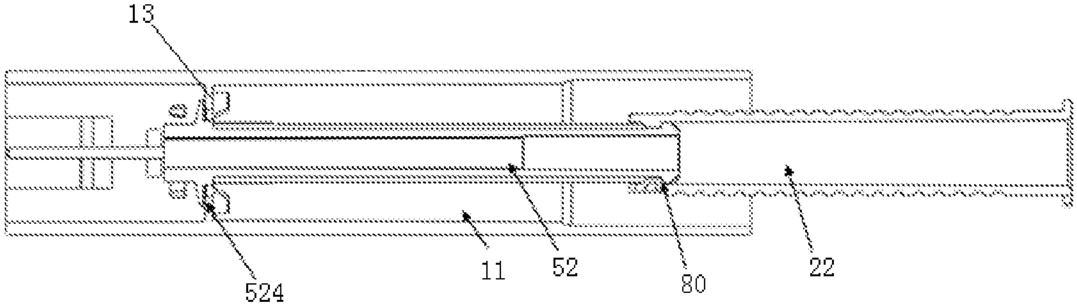
FIG. 15 shows an assembly drawing of the housing, first transmission member and the first memory of the drug delivery device provided in accordance with Embodiment 1 of this application.

As illustrated in FIG. 14, FIG. 15, the first transmission member 52 and the housing 10 are fixed in the axial direction. The first memory 22 is sleeved surrounding the outer surface of first transmission member 52, allowing the first memory 22 to move axially and slidably. The drug delivery device further comprises the second limit structure 80 arranged between the first memory 22 and the first transmission member 52, and the second limit structure 80 can limit the relative position of first memory 22 and first transmission member 52. In the above, the limit function of the second limit structure 80 is for limiting the movement of first memory both circumferentially and axially.

Specifically, the second limit structure 80 comprises the third limit-protrusion 81 and the limit-groove 82, and the third limit-protrusion 81 is provided on one of the first memory 22 and first transmission member 52, and the limit-groove 82 is provided on the other one of the first memory 22 and first transmission member 52, where the limit-groove 82 extends in the axial direction of housing 10. Third limit-protrusion 81 provided within the limit-groove 82, allowing the protrusion 81 to move axially, and third limit-protrusion 81 is cooperated with limit-groove 82 to limit the relative movement of the first memory 22 and first transmission member 52 in both circumferential and axial directions. As the limit-groove 82 extending along the axis of housing 10, and third limit-protrusion 81 is slidably provided within the limit-groove, so the first memory cannot rotate relative to the first transmission member. During the dose setting process by rotating the adjusting member 21 to a desired dose, the first memory will move axially relative to the first transmission member, if adjusting member 21 is adjusted to the scale that is the maximum available dose, the third limit-protrusion will be against end wall 821, thus limiting the axial movement of the first memory, then preventing from continuing adjusting scale in the clockwise direction.

Otherwise, an additional limit-protrusion can be provided within the limit-groove 82, which can also limit the axial movement of the first memory by engaging against the third limit-protrusion 81 during rotation of the adjusting member 21 to the single maximum dose. In the present embodiment, compared to an additional limit-protrusion in the limit-groove, adjusting the length of the limit-groove 82 is able to limit the axial movement of the first memory, which could simplify the structure, ease the operation and lower the costs. Specifically, the limit protrusion works in the same way with the end wall 821 of limit groove, which could be considered as a limit protrusion.

In the present embodiment, the third limit-protrusion 81 is provided on the inner surface of first memory 22 and limit-groove 82 is provided on the outer wall of first transmission member 52. In other embodiments, third limit-protrusion 81 can be provided on the outer surface of first transmission member 52 and limit-groove 82 can be provided on the inner surface of first memory 22.

As illustrated in FIG. 15, in the present embodiment, first ring-protrusion 13 is provided on the inner surface of the housing and second ring-protrusion 524 is provided on the outer surface of first transmission member 52, wherein first ring-protrusion cooperates with the second ring-protrusion in a snap-fit manner to limit the movement of the first transmission member in the axial direction of the housing.

Figure 11:
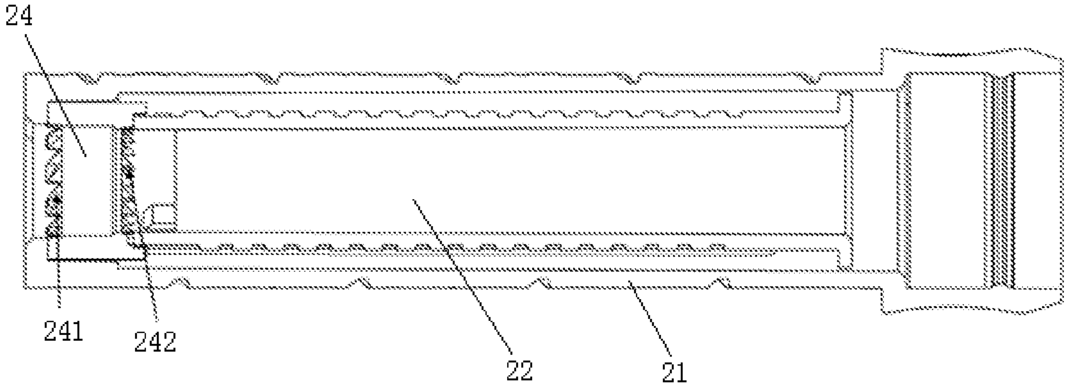
FIG. 11 shows an assembly drawing of the adjusting member, clutch member and first memory of the drug delivery device provided in accordance with Embodiment 1 of this application.
Figure 12:
FIG. 12 shows a structural schematic diagram of the adjusting member in FIG. 1.
Figure 13:
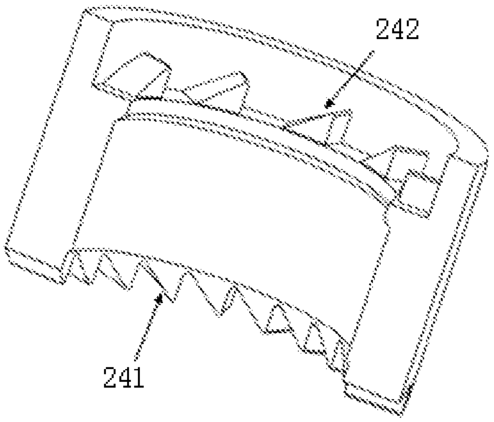
FIG. 13 shows a structural schematic diagram of the clutch member in FIG. 1.

As illustrated in FIG. 11 to 13, driving mechanism 20 also comprises clutch member 24 provided between adjusting member 21 and first memory 22, one end of clutch member 24 is provided with first tooth 241, and the other end of clutch member 24 is provided with second tooth 242. Specifically, adjusting member 21 comprises ring-protrusion 211 arranged along a circumferential direction of adjusting member 21, the side of ring-protrusion 211 facing the clutch member comprises a third tooth 212 engaging with first tooth 241, and the side of first memory 22 facing the clutch member comprises a fourth tooth 221 engaging with the second tooth 242. Furthermore, the teeth of first tooth 241 extend in the same direction as the teeth of second tooth 242. In the above embodiment, the clutch member is a bouncing gear.

As illustrated in FIGS. 3 and 13, in the present embodiment, the teeth of the first tooth 241 extends in the same direction as the teeth of the second tooth 242, specifically, viewed from the same side on the axial direction of clutch member 24, both the teeth of the first tooth 241 and the second tooth 242 extend in the same direction of either clockwise or counterclockwise.

In the above, the parameters such as the shape and number of the teeth of the first teeth 241 and the second teeth 242 can be adjusted according to the requirements. In the present embodiment, the number of the teeth of first teeth 241 is more than the number of teeth of the second teeth 242.

Specifically, adjusting member 21 rotates relative to clutch member 24 when increasing the dose, and clutch 24 rotates relative to the first memory 22 when decreasing the dose, so as to generate audible sound that helps to remind the patients. Moreover, since the teeth of first tooth 241 extend in the same direction as the teeth of second tooth 242, the above two unidirectional bounce are in opposite directions.

Figure 2:
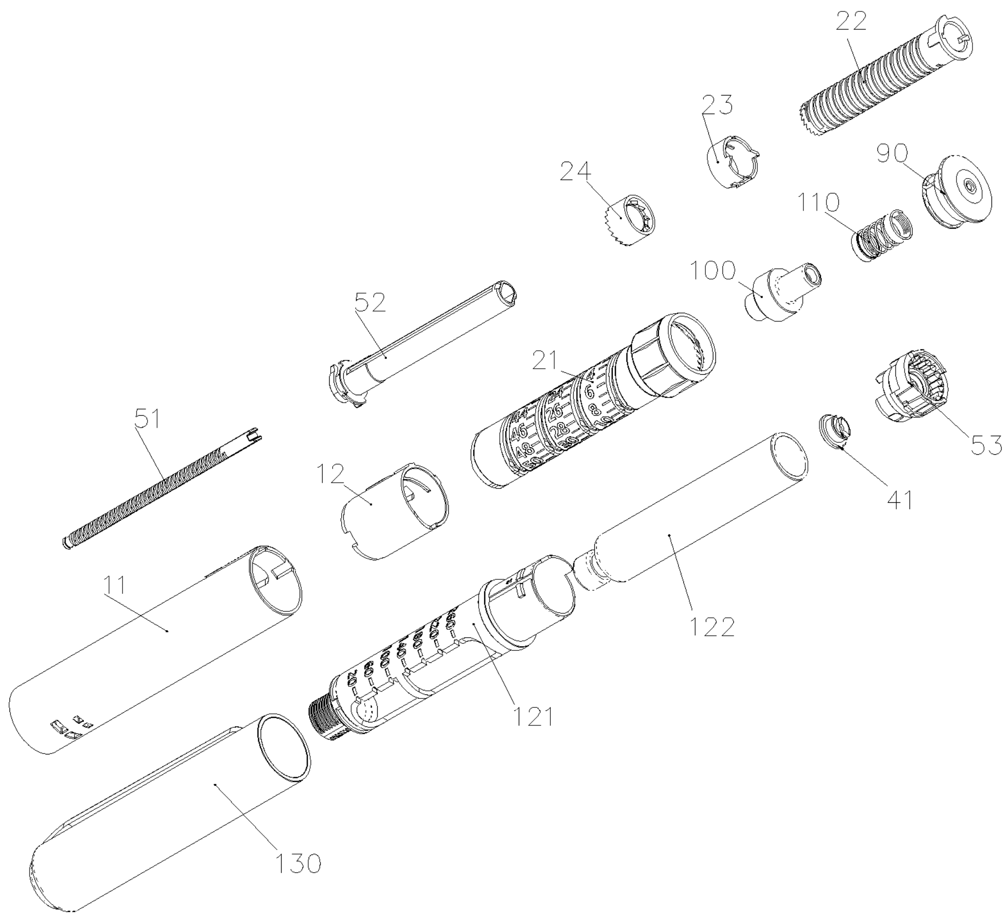
FIG. 2 shows an exploded diagram of the drug delivery device provided in accordance with Embodiment 1 of this application.

As illustrated in FIG. 1 to 3, the drug delivery device further comprises injection button 90, injection button connector 100, resilient member 110 and medication container 120, in the above, injection button 90 is provided at the drive end of the housing 10, injection button connector 100 is provided between the injection button 90 and the first memory 22 within the housing 10, resilient member 110 is provided between injection button 90 and injection button connector 100, and the medication container 120 is provided at the injection end of the housing 10. Specifically, the injection mechanism 40 comprises flange 41, flange 41 being movably provided within the medication container 120, and transmission-mechanism 50 being drivingly connected to flange 41. In the above embodiment, the housing 10 comprises main housing 11 and sleeve 12, both of them are provided separately, to facilitate assembly. In the present embodiment, the resilient member is a spring.

In the present embodiment, the medication container 120 comprises medicine bottle holder 121 and medicine bottle 122, flange 41 is provided inside the medicine bottle, and pen cap 130 is provided outside the medicine bottle holder.

Furthermore, the drive end of the housing refers to the right end in FIG. 1, users can press the button or rotate the adjusting member at the drive end by hand, and the injection end of the housing refers to the left end in FIG. 1, the medicine bottle is provided at the injection end.

Moreover, the screw pitch between the adjusting member and the housing in this drug delivery device is longer than the screw pitch between the piston rod and the second transmission member. In other words, the screw pitch of adjusting member that users directly grip is longer, whereas the crew pitch of piston rod that is used to push the piston within drug container is shorter. The amount of one unit of medication is small, for example, the axial distance in drug container is 0.14 mm for delivering 0.01 ml of medication, so it would require extremely high accuracy if the piston is pushed directly, which is impractical for injection. At present, by using the principle of reducer, users can move about 0.56 mm axially when piston rod which is used to advance the piston moves forward by 1 unit, that is, 0.14 mm. The second part of the thread amplification multiple is 4 times, thus reducing the injection error.

In the present embodiment, the drug delivery device comprises an injection mechanism, in particular a disposable injection pen.

In the above, the specific structure of the injection mechanism and the transmission-mechanism can be changed according to the actual situation, as long as it is possible to ensure that the injection and transmission proceed smoothly.

In the present embodiment, part A is drive connected to part B, meaning that part A drives part B to move, and the movement includes rotational movement and displaceable movement. In the above, part A can be directly drive-connected to part B, and part A can be indirectly drive connected to part B by driving mechanism. For example, piston rod 51 is drive connected to injection mechanism 40, including the end of piston rod 51 being directly connected to flange 41, which directly drives flange 41 to move axially when piston rod 51 is moving in axial direction, thus completing the injection, otherwise, piston rod 51 is connected to flange 41 by an intermediate connector, and piston rod 51 transmits the driving force to flange 41 by the intermediate connector, then drives the flange 41 to move in axial direction.

Embodiment 2 of the present application provides a drug delivery device. The difference between Embodiment 2 and Embodiment 1 is that in Embodiment 2, the end of the first transmission member 52 is provided with a first unidirectional teeth 522, the end wall of the first segment of first transmission member 52 is provided with a reset member 521, and the reset member 521 is provided with a second unidirectional teeth 533. The reset member 521, the first unidirectional teeth 522 and the second unidirectional teeth 533 cooperate to limit the unidirectional rotation of the first transmission member 52 relative to the second transmission member 53.

Specifically, the end wall of the first transmission member 52 is provided with a first unidirectional teeth 522, one end of the reset member 521 is arranged on the end wall of the first segment of the second transmission member 53, and the other end of the reset member 521 is a free end, the second unidirectional teeth 533 is arranged on the free end of the reset member 521, the free end of the reset member 521 can move relative to the second transmission member 53 in the axial direction. The reset member 521, the first unidirectional teeth 522 and the second unidirectional teeth 533 cooperate to limit the unidirectional rotation of the first transmission member 52 relative to the second transmission member 53, that is, the first transmission member 52 can only rotate in one direction of injection relative to the second transmission member 53.

Figure 16:
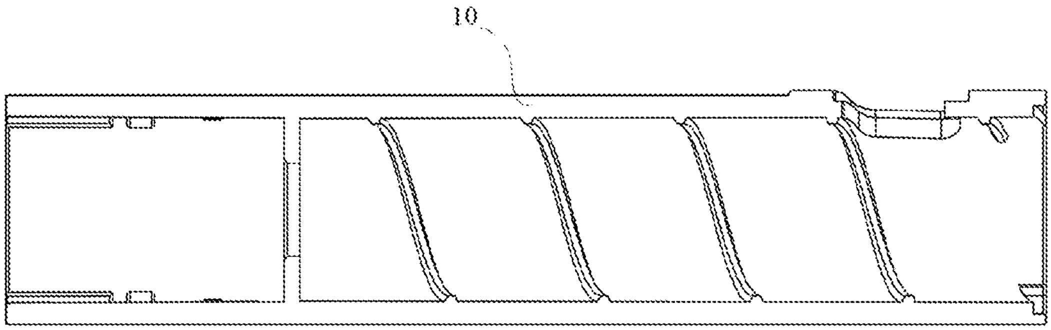
FIG. 16 shows a structural schematic diagram of the housing of the drug delivery device provided in accordance with Embodiment 3 of this application.

As shown in FIG. 16, Embodiment 3 of the present application provides a drug delivery device. The difference between Embodiment 3 and Embodiment 1 is that in Embodiment 3, the main housing 11 and the sleeve 12 are integrally formed, which is convenient for processing and improve the integration of the device.

In order to clearly illustrate the drug delivery device provided in the embodiments, the following will be described in combination with the operational process. The operation method of the drug delivery device comprises:

(1) Increase a dose: screw out the adjusting member 21 (increase the scale), fix the housing, and screw the adjusting member 21 in the clockwise direction. Meanwhile the scale is increasing which can be observed through the window on the housing;

(2) Decrease a dose: screw back the adjusting member 21 (decrease the scale) relative to the housing, the adjusting member can be rotated in the anticlockwise direction if the scale was more than the desired scale. Meanwhile the scale is decreasing.

(3) Injection: When the scale is adjusted to the desired position, hold the housing, press the injection button 90 to push forward, and the force can be transmitted to the adjusting member 21 through the injection button connector 100, the first memory 22 and the clutch member 24, so that the adjusting member 21 bears axial force. Due to the threaded engagement between the adjusting member 21 and the housing 10, the adjusting member 21 rotates, the force of which is finally transmitted to the rotation of the piston rod, so that causing the axial displacement of the piston rod relative to the second transmission member, thus delivering a dose.

Moreover, piston rod cannot move in the process of either increasing or decreasing a dose, and piston rod does not rotate, thus no medication is delivered. Accordingly, users can increase or decrease doses at will.

The device provided by the embodiment has the following beneficial effects:

(1) It has a memory function. Through the cooperation between the first memory and the second memory, when the remaining medication amount of medication container is less than the patient's required injection dose, the patient can only adjust to the remaining medication amount in the medication container, thereby indicating the patient that the dose is insufficient and a new injection pen can be prepared in advance;

(2) It has a unidirectional rotation structure and a function of decreased dose setting;

(3) It has audible feedback structures: it has audible feedback in both increased or decreased dose setting;

(4) Using the cooperation of the third limit-protrusion 81 and the limit-groove 82, it can set a maximum dose in single time;

(5) It is self-administered so that there is no need to see doctor frequently; it has a simple structure, moderate volume and is portable; it allows patients to accurately set a desired dose; compared to traditional syringes, it is more durable; it can reduce pain by controlling injection speed by oneself.

The above descriptions are only preferred embodiments of the present application, and are not intended to limit the present application. For skilled person in the art, there may be various modifications and changes in the present application. Any modifications, equivalent replacements, improvements, etc. made within the spirit and principles of this application shall be included within the protection scope of this application.

What is claimed is:

1. A drug delivery device comprising:

a housing (10);

a driving mechanism (20) arranged in the housing (10), the driving mechanism (20) comprises an adjusting member (21), a first memory (22) and a second memory (23) cooperating with the first memory (22), the second memory (23) has an initial position and an end position relative to the first memory (22), and the driving mechanism (20) has a adjusting state and a delivering state; when the driving mechanism (20) is in the adjusting state, the adjusting member (21) drives the second memory (23) to move between the initial position and the end position; when the driving mechanism (20) is in the delivering state, the adjusting member (21), the first memory (22) and the second memory (23) are relatively static;

a first limiting structure (30) comprising a first limit member (31) and a second limit member (32), one of the first limit member (31) and the second limit member (32) is arranged on the first memory (22), and the other of the first limit member (31) and the second limit member (32) is arranged on the second memory (23); the first limit member (31) cooperates with the second limit member (32) to limit the movement of the second memory (23) relative to the first memory (22) when the second memory (23) is at the end position;

an injection mechanism (40) used for injecting medication; a transmission mechanism (50) arranged between the driving mechanism (20) and the injection mechanism (40), the driving mechanism (20) drives the injection mechanism (40) to inject a dose through the transmission mechanism (50).

2. The drug delivery device according to claim 1, wherein the adjusting member (21) is rotatably and axially movably arranged in the housing (10), the first memory (22) is arranged within the adjusting member (21), the second memory (23) is sleeved on the outer wall of the first memory (22) and is threadedly cooperating with the first memory (22), and a first rotation-preventing structure (60) is arranged between the second memory (23) and the adjusting member (21) to limit the rotation of the second memory (23) relative to the adjusting member (21).

3. The drug delivery device according to claim 2, wherein the first rotation-preventing structure (60) comprises a first rotation-preventing protrusion (61) and a first rotation-preventing groove (62), one of the first rotation-preventing protrusion (61) and the first rotation-preventing groove (62) is arranged on the inner wall of the adjusting member (21), and the other of the first stop protrusion (61) and the first stop groove (62) is arranged on the outer wall of the second memory (23); the first stop protrusion (61) is inserted in the first stop groove (62), and both of the first stop protrusion (61) and the first stop groove (62) extend along the axial direction of the adjusting member (21).

4. The drug delivery device according to claim 1, wherein the first limit member (31) is a first limit protrusion arranged on the one side of the first memory (22) close to the end position, the second limit member (32) is a second limit protrusion arranged on the one the side of the second memory (23) close to the end position, and the first limit protrusion cooperates with the second limit protrusion in a snap-fit manner to limit the rotation of the second memory (23) relative to the first memory (22).

5. The drug delivery device of claim 1, wherein the transmission mechanism (50) comprises: a piston rod (51) drivingly connected to the injection mechanism (40);

a first transmission member (52) rotatably arranged in the housing (10), the driving mechanism (20) is drivingly connected to the first transmission member (52), and the piston rod (51) is arranged within the first transmission member (52); a second rotation-preventing structure (70) is arranged between the piston rod (51) and the first transmission member (52) to limit the rotation of the piston rod (51) relative to first transmission member (52);

a second transmission member (53) fixed in the housing (10), the piston rod (51) is arranged within the second transmission member (53) and threadedly cooperates with the second transmission member (53);

a unidirectional rotation structure (54) arranged between the first transmission member (52) and the second transmission member (53), the unidirectional rotation structure (54) is used to limit the unidirectional rotation of first transmission member (52) relative to the second transmission member (53).

6. The drug delivery device according to claim 5, wherein the second transmission member (53) comprises an opening (531) comprising a first segment and a second segment connected to each other, the second segment is configured to face the first transmission member (52), the first segment is provided with an internal thread (532) cooperated with the piston rod (51), and one end of the first transmission member (52) is arranged within the second segment, wherein, the end of the first transmission member (52) is provided with a reset member (521) provided with a first unidirectional teeth (522), and the inner wall of the second segment is provided with second unidirectional teeth (533); the reset member (521), the first unidirectional teeth (522) and the second unidirectional teeth (533) cooperate to limit the unidirectional rotation of first transmission member (52) relative to the second transmission member (53), or, the end of the first transmission member (52) is provided with a first unidirectional teeth (522), the end wall of the first section is provided with a reset member (521), and the reset member (521) is provided with a second unidirectional teeth (533); the reset member (521), the first unidirectional teeth (522) and the second unidirectional teeth (533) cooperate to limit the unidirectional rotation of the first transmission member (52) relative to the second transmission member (53).

7. The drug delivery device according to claim 5, wherein the first transmission member (52) is axially fixed to housing (10), the first memory (22) is axially and slidably sleeved on the outer wall of the first transmission member (52), and the drug delivery device further comprises:

the second limit structure (80) arranged between the first memory (22) and the first transmission member (52), and the second limit structure (80) is used to limit the position of the memory member (22) relative to the first transmission member (52).

8. The drug delivery device according to claim 7, wherein the second limit structure (80) comprises a third limit protrusion (81) arranged on the one of the first memory (22) and the first transmission member (52) and a limit groove (82) first transmission member set on the other of the first memory (22) and the first transmission member (52), the limit-groove (82) extends along the axial direction of the housing (10), and the third limit protrusion (81) is slidably arranged within the limit groove (82) and cooperates with the limit groove (82) to limit the relative displacement between first memory (22) and the first transmission member (52) in both the circumferential direction and axial direction.

9. The drug delivery device of claim 1, wherein the driving mechanism (20) further comprises a clutch member (24) arranged between the adjusting member (21) and the first memory (22), one end of the clutch member (24) is provided with a first tooth (241), and the other end of the clutch member (24) is provided with a second tooth (242); the adjusting member (21) comprises a ring-protrusion (211) arranged along the circumference of the adjusting member (21), the ring-protrusion (211) is provided with a third tooth (212) engaging with the first tooth (241), and the end wall of first memory (22) is provided with a fourth tooth (221) engaging with the second tooth (242).

10. The drug delivery device of claim 1, wherein the drug delivery device further comprises an button (90) arranged at the driving end of the housing (10), a connector (100) arranged in the housing (10) and between the button (90) and the first memory (22), a resilient member (110) arranged between the button (90) and the connector (100) and a medication container (120) arranged at the injection end of the housing (10);

the injection mechanism (40) comprises a flange (41) movably arranged in the medication container (120), and the transmission mechanism (50) is drivingly connected to the flange (41);

the housing (10) comprises a main housing (11) and a sleeve (12) arranged separately, or the main housing (11) and the sleeve (12) are integrally formed.

11. The drug delivery device according to claim 2, wherein the first limit member (31) is a first limit protrusion arranged on the one side of the first memory (22) close to the end position, the second limit member (32) is a second limit protrusion arranged on the one the side of the second memory (23) close to the end position, and the first limit protrusion cooperates with the second limit protrusion in a snap-fit manner to limit the rotation of the second memory (23) relative to the first memory (22).

12. The drug delivery device according to claim 3, wherein the first limit member (31) is a first limit protrusion arranged on the one side of the first memory (22) close to the end position, the second limit member (32) is a second limit protrusion arranged on the one the side of the second memory (23) close to the end position, and the first limit protrusion cooperates with the second limit protrusion in a snap-fit manner to limit the rotation of the second memory (23) relative to the first memory (22).

* * * * *